United States Patent [19]
Anthony et al.

[11] Patent Number: 5,574,025
[45] Date of Patent: Nov. 12, 1996

[54] INHIBITORS OF PRENYL-PROTEIN TRANSFERASES

[75] Inventors: Neville J. Anthony, Hatfield; Robert P. Gomez, Perkasie; Charles A. Omer, Lansdale, all of Pa.

[73] Assignee: Merck & Co., Inc., Rahway, N.J.

[21] Appl. No.: 329,587

[22] Filed: Oct. 26, 1994

[51] Int. Cl.$^6$ .............. A61K 31/66; C07F 9/40; C07F 9/38; C07F 9/24
[52] U.S. Cl. .......... 514/129; 514/114; 514/119; 514/125; 514/134; 558/155; 558/166; 558/170; 558/177; 558/178; 558/184; 558/189; 558/217; 562/8; 562/11; 562/15; 562/16; 562/20; 562/21; 562/22
[58] Field of Search ................ 562/23, 15, 24; 558/177; 514/119, 129

[56] References Cited

U.S. PATENT DOCUMENTS

| | | |
|---|---|---|
| 3,173,942 | 3/1965 | Barton et al. . |
| 4,259,253 | 3/1981 | Donetti et al. . |
| 4,693,849 | 9/1987 | Mignani et al. . |
| 4,738,801 | 4/1988 | Tahara et al. . |
| 4,837,023 | 6/1989 | Eibl . |
| 4,871,721 | 10/1989 | Biller . |
| 5,043,268 | 8/1991 | Stock . |
| 5,049,552 | 9/1991 | Eibl . |
| 5,202,456 | 4/1993 | Rando .................. 562/23 X |
| 5,274,145 | 12/1993 | Gubelmann .............. 554/213 |
| 5,298,655 | 3/1994 | Anthony et al. . |
| 5,362,906 | 11/1994 | Anthony et al. . |

FOREIGN PATENT DOCUMENTS

| | | |
|---|---|---|
| 0044771 | 1/1982 | European Pat. Off. . |
| 0108565 | 5/1984 | European Pat. Off. . |
| 0356866 | 3/1990 | European Pat. Off. . |
| 0409181A2 | 1/1991 | European Pat. Off. . |
| 0442816A1 | 8/1991 | European Pat. Off. . |
| 0456180A1 | 11/1991 | European Pat. Off. . |
| 0537008A1 | 4/1993 | European Pat. Off. . |
| 0540782 | 5/1993 | European Pat. Off. . |
| 1.981M | 8/1963 | France . |
| 3516114A1 | 11/1986 | Germany . |
| 52-46017 | 4/1977 | Japan . |
| 52-48621 | 4/1977 | Japan . |
| 56-73011 | 6/1981 | Japan . |
| 57-21346 | 2/1982 | Japan . |
| 1-213288 | 8/1989 | Japan . |
| 938712 | 10/1963 | United Kingdom . |
| WO87/03478 | 6/1987 | WIPO . |
| WO91/16340 | 10/1991 | WIPO . |

OTHER PUBLICATIONS

Hoshino, C. et al. *Chemical Abstracts* vol. 95, No. 6382; Argic. Biol. Chem. 1980, 44 (12), 3007–9.
Kimura, K. et al. *Chemcical Abstracts* vol. 87, No. 136066; JP 52–017416, published on Feb. 9, 1977.
Azuma, I. et al., *Vaccine* 1988, 6(4), 339–342.
Derwent Abstract No. 77–20831Y; JP 52–017416, published on Feb. 9, 1977.
C. Field, Pat. Abst Jap., No. 62 142 137:11, No. 369, p. 138 (Dec. 2, 1987).
Schaber, et al., J. Biol. Chem.; 265, No. 25, pp. 14701–14704, (Sep. 5, 1990).
C. Field, Pat. Abst Jap., Unexamined Appl.; 12, No. 84, p. 78 (Mar. 17, 1988).
J. L. Goldstein, J. Biol. Chem.; 266, No. 24, pp. 15575–15578 (1991).
D. L. Pompliano, et al., Biochemistry; 31, p. 3800 (1992).
J. B. Gibbs, et al., J. Biol. Chem.; 268, pp. 7617–7612 (1993).

*Primary Examiner*—Johann Richter
*Assistant Examiner*—Michael G. Ambrose
*Attorney, Agent, or Firm*—David A. Muthard; Mark R. Daniel

[57] ABSTRACT

The compounds disclosed inhibit the prenylation of several proteins. These compounds are potent inhibitors of farnesyl-protein transferase and geranylgeranyl-protein transferase. Further contained in this invention are chemotherapeutic compositions containing these prenyl-transferase inhibitors and methods for their production.

4 Claims, No Drawings

INHIBITORS OF PRENYL-PROTEIN TRANSFERASES

BACKGROUND OF THE INVENTION

Prenylation of proteins by intermediates of the isoprenoid biosynthetic pathway represents a new class of post-translational modification (Glomset, J. A., Gelb, M. H., and Farnsworth, C. C. (1990). *Trends Biochem. Sci.* 15:139–142; Maltese, W. A. (1990). FASEB J. 4:3319–3328). This modification typically is required for the membrane localization and function of these proteins. Prenylated proteins-share characteristic C-terminal sequences including CaaX (C, Cys; a, usually aliphatic amino acid; X, another amino acid), XXCC, or XCXC. Three post-translational processing steps have been described for proteins having a C-terminal CaaX sequence: addition of either a 15 carbon (farnesyl) or 20 carbon (geranylgeranyl) isoprenoid to the Cys residue, proteolytic cleavage of the last 3 amino acids, and methylation of the new C-terminal carboxylate (Cox, A.D. and Der, C. J. (1992a). *Critical Rev. Oncogenesis* 3:365–400; Newman, C. M. H. and Magee, A. I. (1993). *Biochim. Biophys. Acta* 1155:79–96). Some proteins may also have a fourth modification: palmitoylation of one or two Cys residues N-terminal to the farnesylated Cys. Proteins terminating with a XXCC or XCXC motif are modified by geranylgeranylation on the Cys residues and do not require an endoproteolytic processing step. While some mammalian cell proteins terminating in XCXC are carboxymethylated, it is not clear whether carboxymethylation follows prenylation of proteins terminating with a XXCC motif (Clarke, S. (1992). *Annu. Rev. Biochem.* 61 :355–386). For all of the prenylated proteins, addition of the isoprenoid is the first step and is required for the subsequent steps (Cox, A. D. and Der, C. J. (1992a). *Critical Rev. Oncogenesis* 3:365–400; Cox, A. D. and Der, C. J. (1992b) *Current Opinion Cell Biol.* 4:1008–1016).

Three enzymes have been described that catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are found in both yeast and mammalian cells (Clarke, 1992; Schafer, W. R. and Rine, J. (1992) *Annu. Rev. Genet.* 30:209–237). FPTase and GGPTase-I are α/β heterodimeric enzymes that share a common α subunit; the β subunits are distinct but share approximately 30% amino acid similarity (Brown, M. S. and Goldstein, J. L. (1993). *Nature* 366: 14–15; Zhang, F. L.; Diehi, R. E., Kohl, N. E., Gibbs, J. B., Giros, B., Casey, P. J., and Omer, C. A. (1994). *J. Biol. Chem.* 269:3175–3180). GGPTase-II has different a and 13 subunits and complexes with a third component (REP, Rab Escort Protein) that presents the protein substrate to the α/β catalytic subunits. Each of these enzymes selectively uses farnesyl diphosphate or geranylgeranyl diphosphate as the isoprenoid donor and selectively recognizes the protein substrate. FPTase farnesylates CaaX-containing proteins that end with Ser, Met, Cys, Gln, Phe or Ala. GGPTase-I geranylgeranylates CaaX-containing proteins that end with Leu or Phe. For FPTase and GGPTase-I, CaaX tetrapeptides comprise the minimum region required for interaction of the protein substrate with the enzyme. GGPTase-II modifies XXCC and XCXC proteins; the interaction between GGPTase-II and its protein substrates is more complex, requiring protein sequences in addition to the C-terminal amino acids for recognition. The enzymological characterization of these three enzymes has demonstrated that it is possible to selectively inhibit one with little inhibitory effect on the others (Moores, S. L., Schaber, M. D., Mosser, S. D., Rands, E., O'Hara, M. B., Garsky, V. M., Marshall, M. S., Pompliano, D. L., and Gibbs, J. B., *J. Biol. Chem.*, 266:17438 (1991)).

The characterization of protein prenylation biology and enzymology has opened new areas for the development of inhibitors which can modify physiological processes. The prenylation reactions have been shown genetically to be essential for the function of a variety of proteins (Clarke, 1992; Cox and Der, 1992a; Gibbs, J. B. (1991). *Cell* 65:1–4; Newman and Magee, 1993; Schafer and Rine, 1992). This requirement often is demonstrated by mutating the CaaX Cys acceptors so that the proteins can no longer be prenylated. The resulting proteins are devoid of their central biological activity. These studies provide a genetic "proof of principle" indicating that inhibitors of prenylation can alter the physiological responses regulated by prenylated proteins.

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with Lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci. USA*, 87:7541–7545 (1990)).

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with CAAX sequence inhibit Ras farnesylation (Schaber et al., ibid; Reiss et al., ibid; Reiss et al., PNAS, 88:732–736 (1991)). Such inhibitors may inhibit while serving as alternate substrates for the Ras farnesyl-transferase enzyme, or may be purely competitive inhibitors (U.S. Pat. No. 5,141,851, University of Texas).

Recently, it has been demonstrated that certain inhibitors of farnesyl-protein transferase selectively block the processing of Ras oncoprotein intracellularly (N. E. Kohl et al., Science, 260:1934–1937 (1993) and G. L. James et al., Science, 260:1937–1942 (1993).

Certain non-peptide analogs of farneysl diphosphate (FFP) also inhibit farnesyl-protein transferase (Anthony et al., U.S. Pat. No. 5,298,655, (Mar. 29, 1994)). It has also been noted that some non-peptidal analogs of FPP are selective inhibitors of farnesyl-protein transferase (J. B. Gibbs et al., J. Biol. Chem. (1993) 268:7617).

Protein geranylgeranyltransferase type-I (GGTase-I) transfers a geranylgeranyl group from the prenyl donor geranylgeranyl diphosphate to the cysteine residue of substrate proteins containing a C-terminal CAAX-motif in which the "X" residue is leucine or phenylalanine (Clark, 1992; Newman and Magee, 1993). Known targets of GGTase-I include the gamma subunits of brain heterotrimeric G proteins and Ras-related small GTP-binding proteins such as RhoA, RhoB, RhoC, CDC42Hs, Rac1, Rac2, Rap1A and Rap1B (Newman and Magee, 1993; Cox and Der, 1992a). The proteins RhoA, RhoB, RhoC, Rac1, Rac2 and CDC42Hs have roles in the regulation of cell shape (Ridley, A. J. and Hall, A. (1992). Cell 70:389–399; Ridley, A. J., Paterson, H. F., Johnston, C. L., Keikmann, D., and Hall, A. (1992). Cell 70:401–410; Bokoch, G. M. and Der, C. J. (1993). FASEB J. 7:750–759). Rac and Rap proteins have roles in neutrophil activation s (Bokoch and Der, 1993 ).

Activation of growth factor function and Ras function can cause tumor formation. Recently, it was demonstrated that the Rho and Rac proteins transmit intracellular signals initiated by growth factors and by Ras protein (Prendergast, G. C. and Gibbs, J. B. (1993). Adv. Cancer Res. 62:19–64; Ridley and Hall, 1992; Ridley et al., 1992). Specifically, experiments demonstrated that the function of Rho and Rac proteins was required by Ras and growth factors to change cell shape, a biological parameter indicative of cellular transformation and cancer. Since Rho and Rac proteins require geranylgeranylation for function, an inhibitor of GGPTase-I would block the functions of these proteins and be useful as an anticancer agent.

Neutrophil activation is part of the body's inflammatory response. (Haslett, C. et al., Cur. Opinion Immunology, 2:10–18 (1989) Geranylgeranylated Rac and Rap proteins are required for this effect (Bokoch and Der (1993); Abo, A. et al., Nature, 353:668–670 (1991); Knaus, U. G. et al., Science, 254:1512–1515 (1991); Eklund, E. A. et al., J. Biol. Chem. 266:13964–13970 (1991); Quinn, M.T. et al., Nature, 342:198–200 (1989)), so an inhibitor of GGPTase-I will have anti-inflammatory activity.

SUMMARY OF THE INVENTION

The present invention comprises novel compounds that inhibit the prenylation of several proteins. The compounds of the instant invention are potent inhibitors of farnesyl-protein transferase and geranylgeranyl-protein transferase. Further contained in this invention are chemotherapeutic compositions containing these prenyl transferase inhibitors and methods for their production.

The compounds of this invention are illustrated by the formula:

$$\text{(structure)} (CH_2)_n-X-(CH_2)_n-Y$$

DETAILED DESCRIPTION OF THE INVENTION

The compounds of this invention inhibit the prenylation of proteins by the enzymes geranylgeranyl protein transferase and farnesyl-protein transferase. In a first embodiment of this invention, the prenyl-protein transferase inhibitors are illustrated by the formula I:

$$\text{(structure)} (CH_2)_n-X-(CH_2)_n-Y \quad \text{I}$$

wherein:

X is $CH_2$, $CH(OH)C=O$, $CHOR$, $CH(NH_2)$, $CH(NH-COR)$, $O$, $S(O)_p$, $NH$, $NHCO$, $OCNH$, $NHP(O)OH$;

Y is $PO(OR)(OR_1)$ or $CO_2R$;

R is H, $C_1$-$C_6$ alkyl, $CH_2CH_2N^+Me_3A^-$;

$R_1$ is H, $C_1$-$C_6$ alkyl, $CH_2CH_2N^+Me_3A^-$;

n is 0, 1, 2 or 3; and p is 0, 1 or 2;

or the pharmaceutically acceptable salts thereof.

The preferred compound of this invention is as follows: (R,S)-[1-Hydroxy-(E,E,E)-3,7,11,15 tetramethyl-2,6,10,14-hexadecatetraenyl]phosphonic acid The compounds of the present invention may have asymmetric centers and occur as racemates, racemic mixtures, and as individual diastereomers, with all possible isomers, including optical isomers, being included in the present invention. The present invention further includes all disulfides of the claimed compounds, derived from two of the same compounds.

When any variable (e.g., alkyl, R, n, etc.) occurs more than one time in any constituent, its definition on each occurence is independent at every other occurrence. Also, combinations of substituents/or variables are permissible only if such combinations result in stable compounds.

As used herein, the term "alkyl" includes cyclic, branched and straight-chain saturated aliphatic hydrocarbon groups having the specified number of carbon atoms up to 20 carbon atoms. Examples of alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, octyl, nonyl, norbornyl, undecyl, dodecyl, tridecyl, tetradecyl, pentadecyl, eicosyl, 3,7-diethyl-2,2-dimethyl-4-propylnonyl, cyclododecyl, adamantyl, and the like.

The term "A" as used herein represents a pharmaceutically acceptable anion.

The pharmaceutically acceptable salts of the compounds of this invention include the conventional non-toxic salts of the compounds of this invention as formed, e.g., from non-toxic salts or the quaternary ammonium salts of the compounds of this invention as formed, e.g., from non-toxic inorganic or organic bases.

The pharmaceutically acceptable salts of the acids of the present invention are readily prepared by conventional procedures such as treating an acidic compound of this invention with an appropriate amount of a base, such as an alkali or alkaline earth metal hydroxide, e.g., sodium, potassium, lithium, calcium or magnesium, or an organic base such as an amine, e.g., dibenzylethylenediamine, benzylamine and the like, or a quaternary ammonium hydroxide such as tetramethylammonium hydroxide and the like.

Abbreviations used in the description of the chemistry and in the Examples that follow are:

| | |
|---|---|
| Ac$_2$O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide hydrochloride; |
| HOBT | 1-Hydroxybenzotriazole hydrate; |
| Et$_3$N | Triethylamine; |
| EtOAc | Ethyl acetate; |
| FAB | Fast atom bombardment; |
| HOOBT | 3-Hydroxy-1,2,3-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Synopsis of Reaction Schemes

Compounds of this invention are prepared by employing the reactions shown in the following Reaction Schemes, in addition to other standard manipulations such as ester hydrolysis, cleavage of protecting groups, etc., as may be known in the literature or exemplified in the experimental procedures.

In Reaction Scheme 1, geranylgeraniol was oxidized with manganese dioxide in methylene chloride to yield geranylgeranyal. This aldehyde was treated with dimethyl trimethylsilyl phosphite at 80° C. to afford the α-siloxyphosphonate adduct. Exposure of the phosphonate to trimethylsilylbromide, aqueous workup and preparative HPLC purification afforded the desired α-hydroxyphosphonic acid.

REACTION SCHEME 1

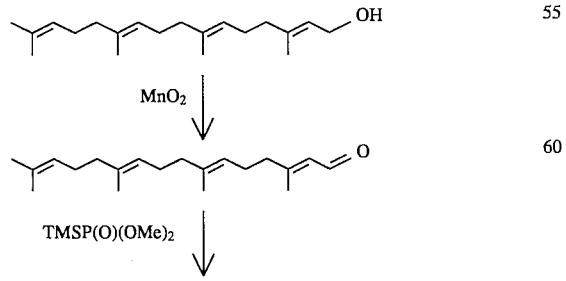

REACTION SCHEME 1
-continued

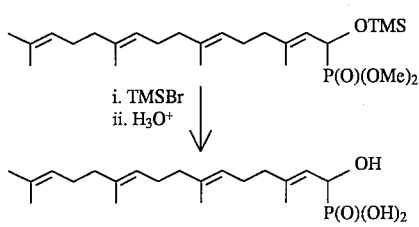

REACTION SCHEME 2

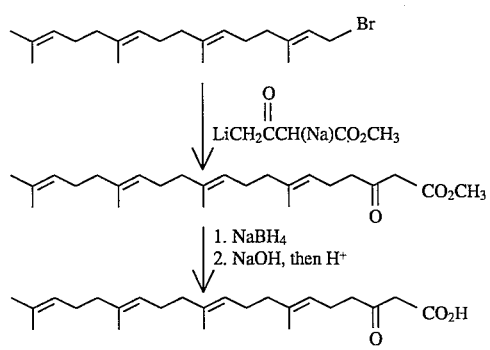

REACTION SCHEME 3

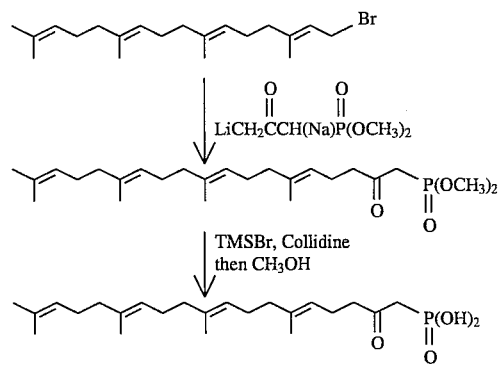

REACTION SCHEME 4

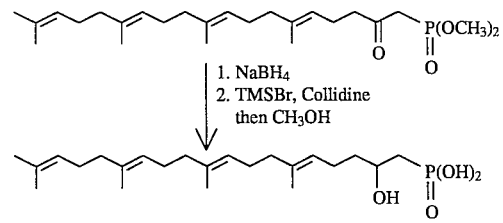

7
REACTION SCHEME 5
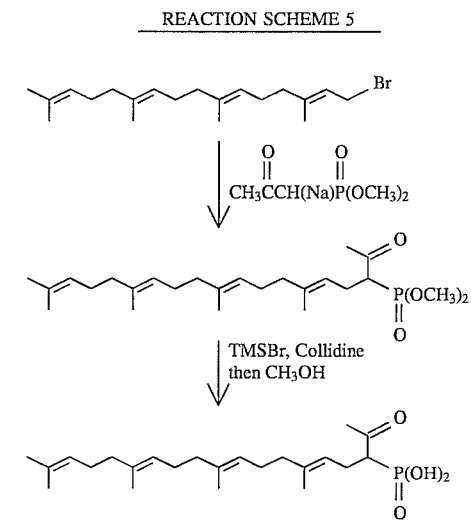
REACTION SCHEME 6
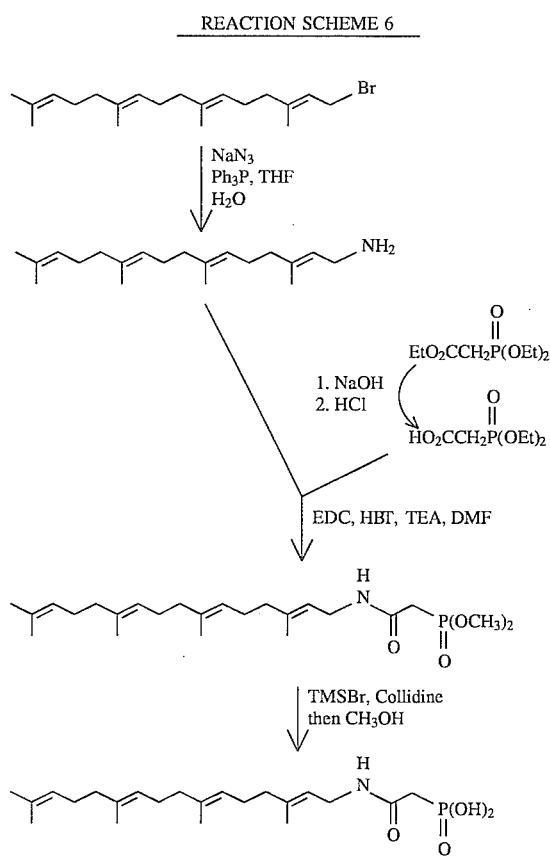
8
REACTION SCHEME 7A
REACTION SCHEME 7B
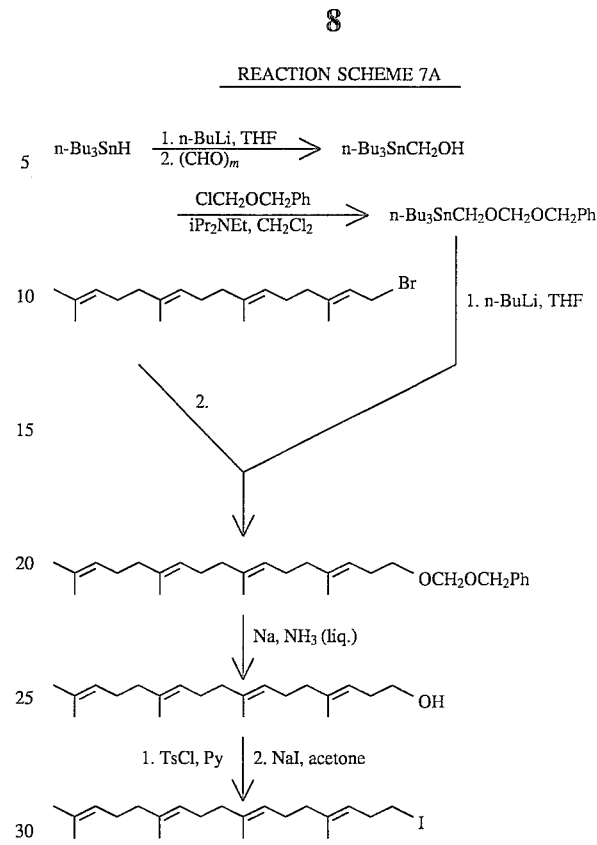

5,574,025
REACTION SCHEME 8
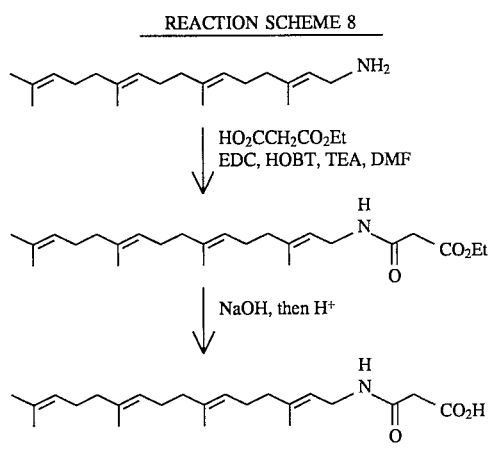
REACTION SCHEME 9
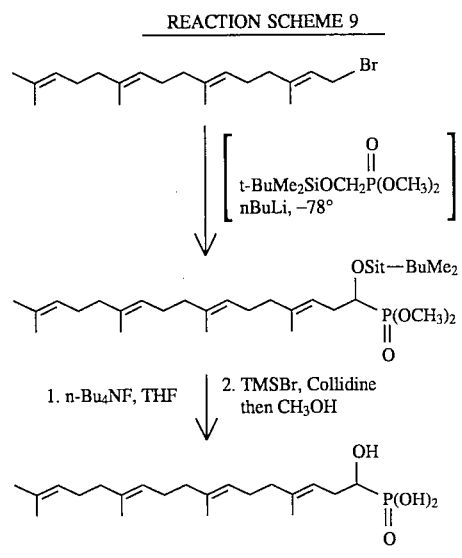
REACTION SCHEME 10A
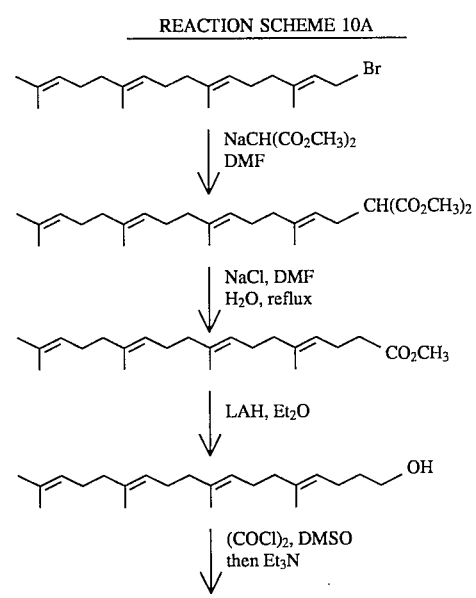
REACTION SCHEME 10B
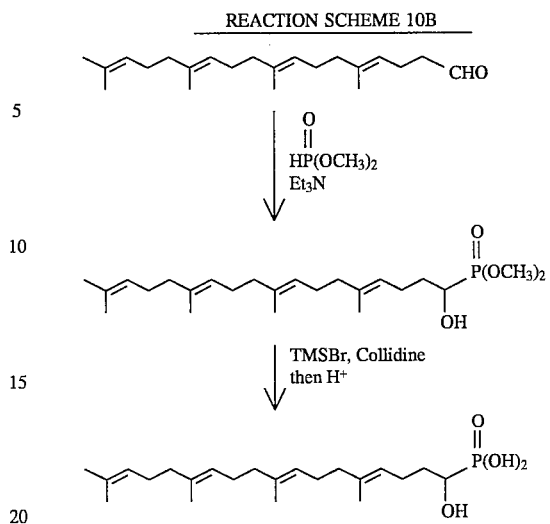
REACTION SCHEME 11
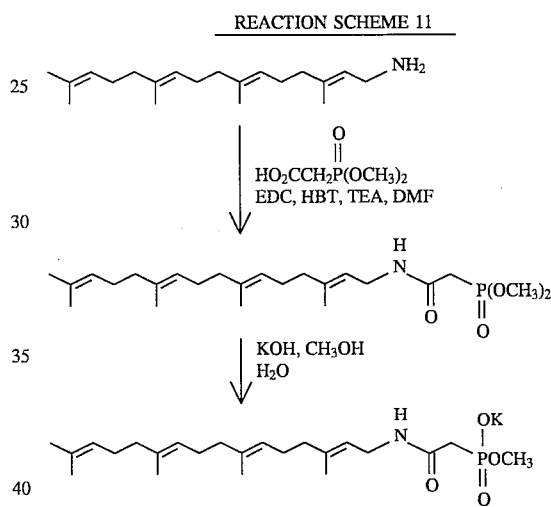
REACTION SCHEME 12
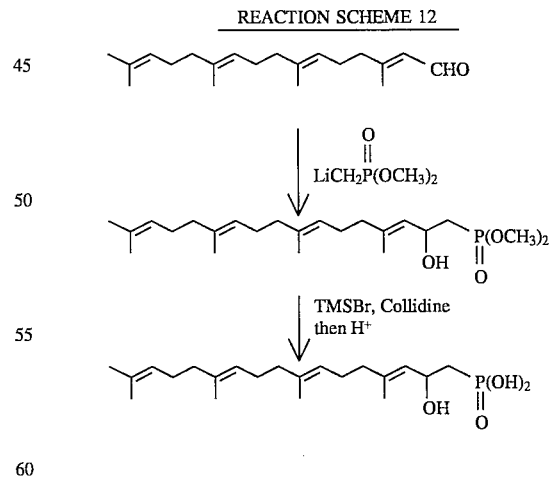

REACTION SCHEME 13

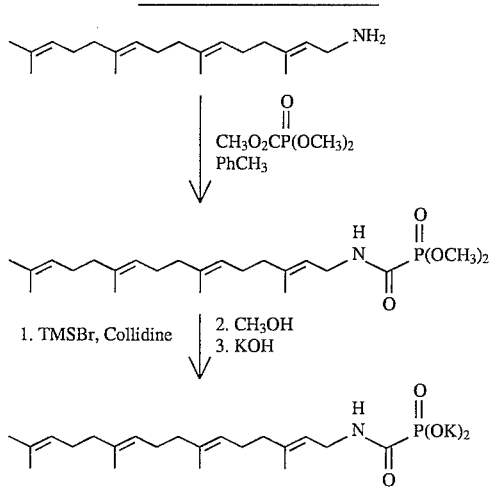

REACTION SCHEME 14

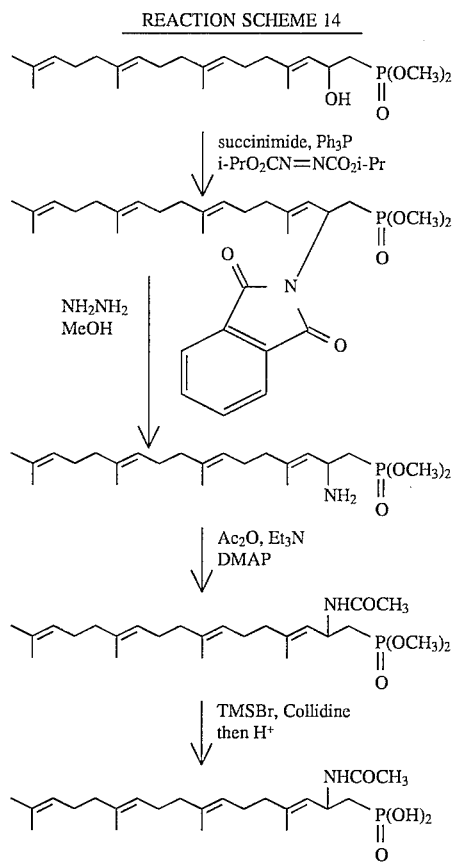

The compounds of this invention inhibit geranylgeranyl-protein transferase and farnesyl-protein transferase, which catalyze the first step in the post-translational processing of several proteins. These compounds are useful as pharmaceutical agents for mammals, especially for humans. These compounds may be administered to patients for use in the treatment of abnormal cellular proliferative diseases and cancer. Such cancers include but are not limited to growth factor stimulated cancers, such as breast carcinomas activated by erb B2, and the like, and Ras regulated cancers, such as colon cancer, pancreatic cancer and the like. The compounds of the instant invention may furthermore be administered to patients for use in the treatment of inflammatory diseases which are regulated by NAPDH oxidase, those diseases in which tissue damage is mediated by phagocytes (neutrophils, macrophages, eosinophils). Such inflammatory diseases include rheumatoid arthritis, inflammatory bowel disease, interstitial pulmonary edaema, myocardial infarction, cystic fibrosis and the like.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of certain cancers and inflammatory diseases comprising the administration of a therapeutically effective amount of the compounds of this invention, with or without pharmaceutically acceptable carders or diluents. Suitable compositions of this invention include aqueous solutions comprising compounds of this invention and pharmacologically acceptable carders, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

In another exemplary application, a suitable amount of compound is administered to a mammal undergoing treatment for an inflammatory disease. The magnitude of prophylactic or therapeutic dose of a compound of Formula I will, of course, vary with the nature of the severity of the condition to be treated and with the particular compound of Formula I and its route of administration. In general, for anti-inflammatory use, administration occurs in an amount between about 0.1 mg/kg of body weight to about 100 mg/kg of body weight per day, preferably of between 0.5 mg/kg of body weight to about 10 mg/kg of body weight per day. On the other hand, it may be necessary to use dosages outside these limits in some cases.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

Example 1

Preparation of (E,E,E)-3,7,11,15 tetramethyl-2,6,10,14-hexadecatetraenal (1)

To a solution of (E,E,E)-3,7,11,15 tetramethyl-2,6,10,14-hexadecatetraen-1-ol (320 mg, 1.1 mmol) in dry methylene chloride (10 ml) at room temperature was added manganese dioxide (957 mg, 0.011 mol) and the resulting mixture stirred for 16 hours. The solids were removed by filtration through a pad of celite washing with methylene chloride (50 ml). The resulting solution was evaporated in vacuo to afford the aldehyde (1) as a clear colorless oil.

$^1$H NMR (CHCl$_3$) δ 1.61 (6H, s), 1.62 (3H, s), 1.69 (3H, s), 1.0–2.22 (10H, m), 2.24 (3H, br s), 2.24–2.35 (2H, m), 5.19 (3H, m), 5.90 (1H, dd, J=8 and 1 Hz), 10.01 (1H, d, J=6 Hz).

Example 2

Preparation of Dimethyl-(R,S)-[1-trimethylsiloxy-(E,E,E)-3,7,11,15-tetramethyl-2,6,10,14-hexadecatetraenyl]phosphonate (2)

To the aidehyde (1) (296 rag, 1.026 mmol) under argon was added the dimethyl trimethylsilyl phosphite (0.196 mL, 1.026 mmol). The resulting mixture was stirred at 80° C. for 6 hours, and then cooled to room temperature to afford the α-trimethylsiloxy dimethyl phosphonate (2) as a clear oil, which was used in the next step without further purification.

$^1$H NMR (CHCl$_3$) δ 0.01 (9H, s), 1.62 (6H, s), 1.90–2.30 (12H, m), 3.80. (3H, d, J=12.5 Hz), 3.83 (3H, d, J=12.5 Hz), 4.70 (1H, t, J=8 Hz), 5.10 (3H, m), 5.90 (1H, br t, J=8 Hz).

Example 3

Preparation of L-752,573 (R,S)-[1-Hydroxy-(E,E,E)-3,7,11,15 tetramethyl-2,6,10,14-hexadecatetraenyl]phosphonic acid (3)

Trimethylsilyl bromide (0.5 ml, 3.78 mmol) was added to a stirred solution of the α-trimethylsiloxy dimethyl phosphonate (2) (0.14 g, 0.29 mmol) and 2,4,6-collidine (0.5 ml, 3.78 mmol) in dichloromethane (5 ml) under argon at 0° C. The resulting mixture was stirred at 0° C. for 30 min. and then at room temperature for 18 hours. The solvent was evaporated in vacuo and excess trimethylsilyl bromide was removed by dilution with toluene and evaporation. The residue was partitioned between ethyl acetate (10 ml) and water (10 ml) and the pH was adjusted to 3 by addiiton of 1M HCl. The organic layer was separated, dried (MgSO$_4$) and the solvent evaporated to afford a yellow semi solid. This residue was further purified by preparative HPLC and lyophilized to afford the α-hydroxy phosphonic acid (3) as a white solid.

$^1$H NMR (CH$_3$OD) δ 1.58 (6H, s), 1.61 (3H, s), 1.66 (3H, s), 1.73 (3H, s), 1.9–2.22 (12H, m), 4.53 (1H, dd, J=10.5 Hz), 4.95–5.2 (3H, m), 5.32 (1H, t, J=7 Hz). Analysis calculated % for C$_{20}$H$_{35}$O$_4$P•0.6 H$_2$O and 0.10 TFA: C, 61.79; H, 9.32. Found %: C, 61.79; H, 9.27.

Transferase Assays. Isoprenyl-protein transferase activity assays were carded out at 30° C. unless noted otherwise. A typical reaction contained (in a final volume of 50 μL): [$^3$H]famesyl diphosphate or [$^3$H]geranylgeranyl diphosphate, Ras protein, 50 mM HEPES, pH 7.5, 5 mM MgCl$_2$, 5 mM dithiothreitol and isoprenyl-protein transferase. The FPTase employed in the assay was prepared by recombinant expression as described in Omer, C. A., Kral, A. M., Diehi, R. E., Prendergast, G. C., Powers, S., Allen, C. M., Gibbs, J. B. and Kohl, N. E. (1993) *Biochemistry* 32:5167–5176. The human GGPTase Type I employed was prepared by recombinant expression as described in *cDNA Cloning and Expression of Rat and Human Protein Geranylgeranyltransferase Type-I* (Zhang, F. L., Diehl, R. E., Kohl, N. E., Gibbs, J. B., Giros, B., Casey, P. J., and Omer, C. A. (1994). *J. Biol. Chem.* 269:3175–3180). After thermally pre-equilibrating the assay mixture in the absence of enzyme, reactions were initiated by the addition of isoprenyl-protein transferase and stopped at timed intervals (typically 15 min) by the addition of 1M HCl in ethanol (1 mL). The quenched reactions were allowed to stand for 15 m (to complete the precipitation process). After adding 2 mL of 100% ethanol, the reactions were vacuum-filtered through Whatman GF/C filters. Filters were washed four times with 2 mL aliquots of 100% ethanol, mixed with scintillation fluid (10 mL) and then counted in a Beckman LS3801 scintillation counter.

For inhibition studies, assays were run as described above, except inhibitors were prepared as concentrated solutions in 100% dimethyl sulfoxide and then diluted 20-fold into the enzyme assay mixture. IC$_{50}$ values were determined with both transferase substrates near K$_M$ concentrations. Nonsaturating substrate conditions for inhibitor IC$_{50}$ determinations were as follows: FTase, 650 nM Ras-CVLS, 100 nM famesyl diphosphate; GGPTase-I, 500 nM Ras-CAIL, 100 nM geranylgeranyl diphosphate.

The compounds of the instant invention were tested for inhibitory activity against human FPTase and human GGPTase by the assay described above and were found to have IC$_{50}$ of <10 μM.

Example 4

In vivo ras famesylation assay

The cell line used in this assay is a v-ras line derived from either Rat 1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 5

In vivo growth inhibition assay

To determine the biological consequences of FPTase inhibition, the effect of the compounds of the instant invention on the anchorage-independent growth of Rat 1 cells transformed with either a v-ras, v-raf, or v-mos oncogene is tested. Cells transformed by v-Raf and v-Mos may be included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium a containing 0.1% methanol or the concentration of the instant compound. Photomicrographs are taken 16 days after the cultures are seeded and comparisons are made.

What is claimed is:

1. A compound which inhibits geranylgeranyl protein transferase type I having the formula I:

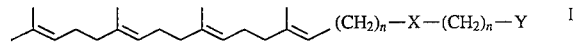

wherein:

X is $CH_2$, $CH(OH)C=O$, CHOR, $CH(NH_2)$, CH(NH-COR), NH, NHCO, OCNH, NHP(O) OH;

p is 0, 1 or 2;

Y is $PO_3$ $RR_1$;

R is H, lower alkyl, $CH_2CH_2N^+ME_3A^-$;

$R_1$ is H, lower alkyl, $CH_2CH_2N^+Me_3A^-$;

A is a pharmaceutically acceptable anion;

n is 0, 1, 2 or 3;

or the pharmaceutically acceptable salts thereof.

2. A compound which inhibits geranylgeranyl-protein transferase and farnesyl-protein transferase which is: (R,S)-[1-Hydroxy-(E,E,E)-3,7,11,15 tetramethyl-2,6,10,14-hexadecatetraenyl]phosphonic acid

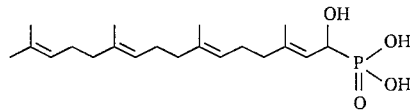

or a pharmaceutically acceptable salt thereof.

3. A pharmaceutical composition comprising a therapeutically effective amount of a compound of claim 1 and a pharmaceutically acceptable carrier.

4. A pharmaceutical composition comprising a therapeutically effective amount of a compound of claim 2 and a pharmaceutically acceptable carrier.

* * * * *